United States Patent [19]

Van der Knaap

[11] Patent Number: Plant 6,340

[45] Date of Patent: Oct. 18, 1988

[54] KALANCHOE PLANT NAMED FUJI

[75] Inventor: Jacques C. M. Van der Knaap, De Lier, Netherlands

[73] Assignee: Fides Beheer B.V., De Lier, Netherlands

[21] Appl. No.: 937,410

[22] Filed: Dec. 3, 1986

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Schwartz, Jeffery, Schwaab, Mack, Blumenthal & Evans

[57] ABSTRACT

A new and distinct cultivar of Kalanchoe plant named Fuji characterized by its bicolored yellow to golden-yellow flowers, compact and free branching habit, floriferous habit, and by its adaptability to produce in 10 to 15 cm pots.

1 Drawing Sheet

The present invention relates to a new and distinctive cultivar of Kalanchoe plant, botanically known as Kalanchoe, and referred to by the cultivar name Fuji.

The new cultivar was referred to during the breeding and selection process by the designation FK83-108, and is a product of a planned breeding program. The basic objective of the breeding program was to create a new Kalanchoe cultivar having mixed yellow and yellow-orange flowers, compact habit, short flowering response and good keeping quality.

Fuji was originated by applicant from a cross made in a controlled breeding program in De Lier, Holland. The female, or seed parent was a cultivar designated Yellow Nugget, disclosed in U.S. Plant Pat. No. 4,726. The male, or pollen parent was the cultivar designated 81-0885.

Fuji was discovered and selected by applicant as a flowering plant within the progeny of the stated cross in a controlled environment in De Lier, Holland. Asexual reproduction of the new cultivar by stem cuttings, as performed by me at De Lier, Holland, has demonstrated that the combination of characteristics as herein disclosed for the new cultivar are firmly fixed and are retained through successive generations of asexual reproduction.

Fuji has not been observed under all possible environmental conditions. The phenotype may vary significantly with variations in environment such as temperature, light intensity and day length. The following observations, measurements and values describe the new cultivar as grown in Parrish, Fla., under greenhouse conditions which closely approximate those generally used in commercial practice.

The following traits have been repeatedly observed and are determined to be basic characteristics of Fuji, which in combination distinguish this Kalanchoe as a new and distinct cultivar:

1. General tonality of flower color at 3 feet is yellow. Closer observation reveals a mixture of yellow and yellow-gold flowers.
2. Compact habit and average growth rate.
3. Freely branching, with shoots formed at every node.
4. Suitable for production in 10–15 cm pots, and flowering in 12–13 weeks using photoperiodic control.
5. Very floriferous, with numerous flowers formed at every node.
6. Responds to B-9 applications to control height.

7. Medium-small sized leaves that are very thick and persistent.

The new cultivar is most similar to the cultivar Fortyniner. Chart A compares certain characteristics of both Fortyniner and Fuji. Fuji is principally distinguished from Fortyniner by its better growth habit, slightly larger flowers, more golden yellower flower color, and earlier flowering.

The accompanying photographic drawing shows a typical specimen plant of the new cultivar. The photograph is in black and white, with certain flowers being colored in an effort to obtain accurate color depiction. However, the bicolored flower makes completely accurate color depiction virtually impossible.

In the following description, color references are made to The Royal Horticultural Society Colour Chart (RHS), except where general colors of ordinary significance are referred to. Color values were taken under fluorescent light conditions in September in Parrish, Fla.

Botanical classification: Kalanchoe, cv. Fuji.

Parentage:

*Male parent.*—81-0885.

*Female parent.*—Yellow Nugget.

Propagation: The new cultivar holds its distinguishing characteristics through successive propagations by leaf cuttings and by division of shoots.

(A) *Type cutting.*—Shoot tip.

(B) *Time to root.*—10–14 days at 21° C.

(C) *Rooting habit.*—Fibrous, many very fine roots.

Plant description:

(A) *Form.*—Upright, short compact growth. Scheduling practices can produce small plants in 10 cm pots and larger plants in 15 cm pots.

(B) *Habit of growth.*—Average rate for this type of plant. Shoots are formed at every node.

(C) *Foliage description.*—Leaves simple, opposite, ovate with unevenly crenate margins. (1) Size: 5–13 cm long. 5–10 cm wide. (2) Shape: Ovate. (3) Texture: Smooth, waxy and succulent. (4) Margin: Unevenly crenate. (5) Color: Young and mature foliage, top side 147A, under side 147B.

Flowering description:

(A) *Flowering habit.*—Compound dichasial cyme on strong peduncles. Peduncle length depends on growing conditions and B-9 applications Pedicles up to 5 mm long.

(B) *Natural flowering season.*—Fall. Flowering time under controlled day length at 75°-85° F. in summer is 13-15 weeks; in winter at 62°-70° F., 12 weeks. Flowering time depends on temperature, light intensity and other growing conditions.

(C) *Flower buds.*—Oblong, developing to tubular as petals mature, sheathed with four green sepals. Corolla at maturity about 10-14 mm long. (1) Size: 10-14 mm long. (2) Shape: Oblong. (3) Rate of opening: Normal.

(D) *Flowers borne.*—Compound dichasial cyme on strong peduncles. Peduncle length depends on growing conditions and B-9 applications. Pedicles up to 5 mm long.

(E) *Quantity of flowers.*—Very floriferous, with new buds continuing to develop.

(F) *Petals.*—(1) Shape: Corolla funnel shaped, petal apex abruptly acuminate. (2) Color: Top side when opening, ranging from 9B to 13A to 22A, fading to colors ranging from 9C to 13C to 22C; under side, ranging from 9D to 13C to 22C. (3) Number and size of petals: Four (4), petals 7 mm in diameter; total flower diameter 16-18 mm.

(G) *Reproductive organs.*—(1) Stamens: Eight (8) in number. (a) Anther shape: Flat, elliptical. (b) Filament color: Yellow. (c) Pollen color: Yellow. (2) Pistels (a) Stigma shape: Flat, crystalline. (b) Style color: Greenish white. (c) Ovaries: 4-celled, cu. 7 mm long, green.

Disease resistance: No known Kalanchoe diseases observed to date.

General observations: Fuji is characterized by its flowers of different shades mixed together on the same plant, with colors ranging from yellow to golden-yellow to generally butterscotch. The bicolor flowers, compact habit and early flowering make Fuji an attractive new cultivar.

CHART A

Fuji vs. Fortyniner
Summer Conditions

| | Fuji | Fortyniner |
|---|---|---|
| Mature flower color | Bicolor ranges 9B/13A/22A | Solid 8A |
| Flowering plant height | 26 cm | 22 cm |
| Weeks to flower | 13 | 14 |
| Mature leaf width | Up to 8 cm | Up to 8.5 cm |
| Mature leaf length | Up to 12 cm | Up to 13 cm |
| Diameter of Flower | 18 mm | 17 mm |

The plants of Fuji and Fortyniner which were used in this comparison were grown together on the same bench in a greenhouse in Parrish, Fla. The color readings were taken under fluorescent light at 2:00 pm on Sept. 17, 1986.

I claim:

1. A new and distinct cultivar of Kalanchoe plant named Fuji, as described and illustrated, and particularly characterized by its bicolored yellow to golden-yellow flowers, compact and free branching habit, floriferous habit, and by its adaptability to produce in 10 to 15 cm pots.

* * * * *

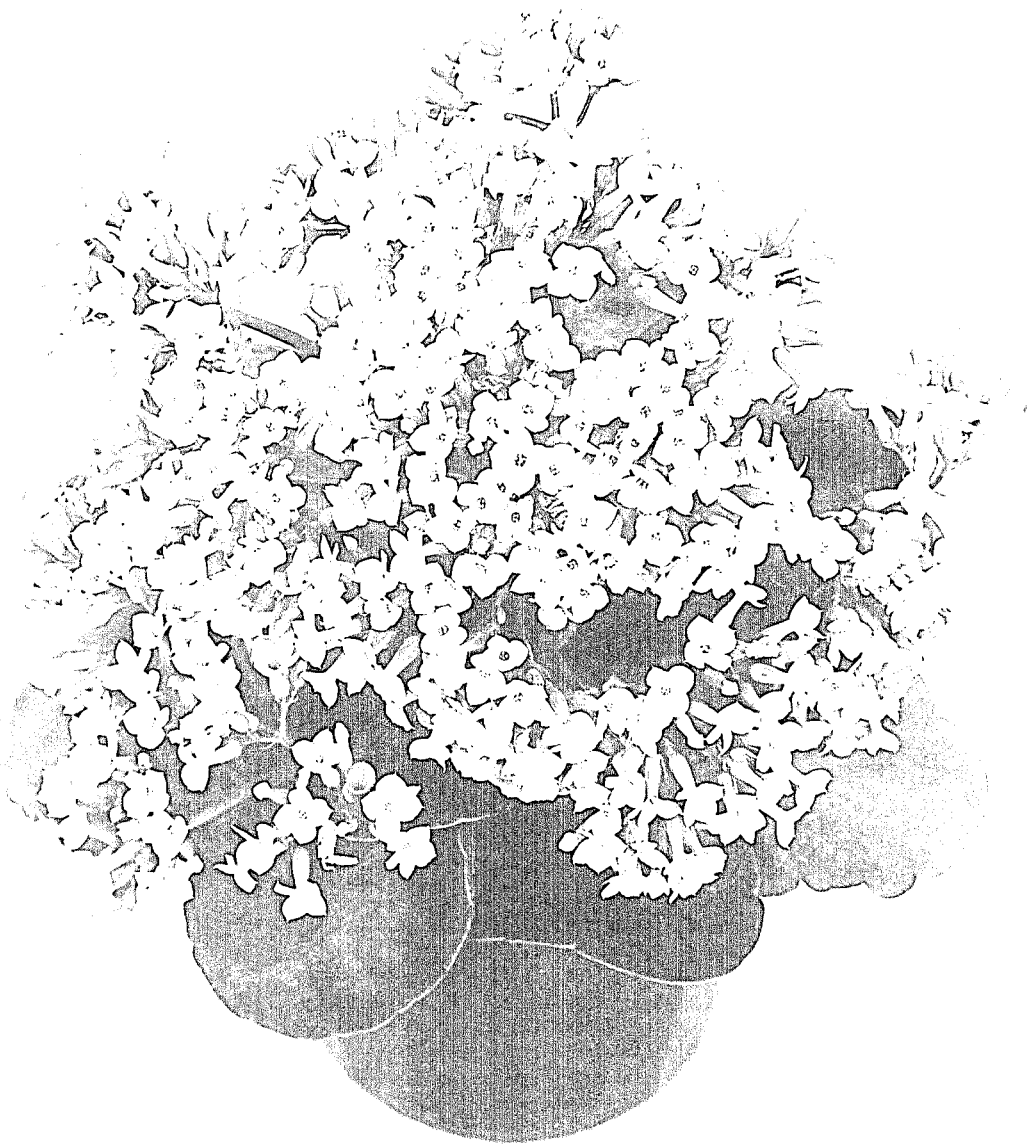

UNITED STATES PATENT AND TRADEMARK OFFICE

CERTIFICATE OF CORRECTION

PATENT NO. : Plant 6,340

DATED : October 18, 1988

INVENTOR(S) : Jacques C. M. Van der Knaap

It is certified that error appears in the above-identified patent and that said Letters Patent is hereby corrected as shown below:

On the Title Page,
Item [73], should read:

Ball Seed Company, West Chicago, Illinois

Signed and Sealed this

Twenty-seventh Day of June, 1989

*Attest:*

DONALD J. QUIGG

*Attesting Officer*

*Commissioner of Patents and Trademarks*